(12) United States Patent
Auner et al.

(10) Patent No.: US 6,853,075 B2
(45) Date of Patent: Feb. 8, 2005

(54) SELF-ASSEMBLED NANOBUMP ARRAY STUCTURES AND A METHOD TO FABRICATE SUCH STRUCTURES

(75) Inventors: Gregory W. Auner, Livonia, MI (US); Ratna Naik, Ann Arbor, MI (US); Simon Ng, West Bloomfield, MI (US); Gary W. Abrams, Ann Arbor, MI (US); James Patrick McCallister, Woodhaven, MI (US); Raymond Iezzi, Troy, MI (US)

(73) Assignee: Wayne State University, Detroit, MI (US)

( * ) Notice: Subject to any disclaimer, the term of this patent is extended or adjusted under 35 U.S.C. 154(b) by 0 days.

(21) Appl. No.: 10/353,756

(22) Filed: Jan. 28, 2003

(65) Prior Publication Data

US 2004/0145053 A1 Jul. 29, 2004

(51) Int. Cl.$^7$ .............................................. H01L 23/48
(52) U.S. Cl. .............................. 257/737; 257/4; 257/5; 257/738
(58) Field of Search .............................. 257/4, 5, 737, 257/738

(56) References Cited

U.S. PATENT DOCUMENTS

| | | | |
|---|---|---|---|
| 4,189,516 A | 2/1980 | Dryburgh et al. |
| 4,265,124 A | 5/1981 | Lim et al. |
| 4,511,816 A | 4/1985 | Mikoshiba et al. |
| 4,937,454 A | 6/1990 | Itoh et al. |
| 5,109,844 A | 5/1992 | de Juan, Jr. et al. |
| 5,155,364 A | 10/1992 | Fujii |
| 5,229,569 A | 7/1993 | Miyauchi et al. |
| 5,343,107 A | 8/1994 | Shikata et al. |
| 5,354,980 A | 10/1994 | Rappoport et al. |
| 5,385,862 A | 1/1995 | Moustakas |
| 5,456,797 A | 10/1995 | Weber et al. |
| 5,464,984 A | 11/1995 | Cox et al. |
| 5,510,481 A | 4/1996 | Bednarski et al. |
| 5,677,538 A | 10/1997 | Moustakas et al. |
| 5,935,155 A | 8/1999 | Humayun et al. |
| 5,936,247 A | 8/1999 | Lange et al. |
| 5,944,747 A | 8/1999 | Greenberg et al. |
| 5,992,215 A | 11/1999 | Caron et al. |
| 6,084,503 A | 7/2000 | Ruile et al. |
| 6,137,231 A | 10/2000 | Anders et al. |
| 6,144,332 A | 11/2000 | Reindl et al. |
| 6,243,517 B1 | 6/2001 | Deacon |
| 6,282,357 B1 | 8/2001 | Kadota et al. |
| 6,312,568 B2 | 11/2001 | Wilke et al. |
| 6,450,008 B1 | 9/2002 | Sunshine et al. |
| 6,501,107 B1 | 12/2002 | Sinclair et al. |
| 6,518,637 B1 | 2/2003 | Thompson et al. |
| 6,567,753 B2 | 5/2003 | Potyrailo |
| 2001/0054305 A1 | 12/2001 | Banda et al. |
| 2002/0008191 A1 | 1/2002 | Faska et al. |
| 2003/0052701 A1 | 3/2003 | Brown et al. |

OTHER PUBLICATIONS

D.S. Ballantine et al., "Acoustic Wave Sensor—Theory, Design, and Physico–Chemical Applications", *Academic Press* (1997).

C. Caliendo et al., "Piezoelectric AlN Film for SAW Device Applications", *Proc. IEEE Ultrasonic Symp.*, 249–252 (1992).

K. Kaya et al., "Synthesis of AlN Thin Films on Sapphire Substrates by Chemical Vapor Deposition of AlCl$_3$—NH$_3$ Systems and Surface Acoustic Wave Properties", *Jpn. J. Appl. Phys.*, vol. 35, 2782–2787, (1996).

(List continued on next page.)

*Primary Examiner*—Fetsum Abraham
(74) *Attorney, Agent, or Firm*—Kenyon & Kenyon

(57) ABSTRACT

A self-assembled nanobump array structure including a semi-absorbing outer layer provided on at least one nanobump-forming substrate layer, the semi-absorbing outer layer configured to ablate slowly to allow an applied laser energy to be transmitted to the at least one nanobump-forming substrate layer, in which the self-assembled nanobump array structure is formed by an energy and a pressure buildup occurring in the at least one nanobump-forming substrate layer.

34 Claims, 14 Drawing Sheets

OTHER PUBLICATIONS

G. Carlotti et al., "The Elastic Constants of Sputtered AlN Films", *Proc. IEEE Ultrasonic Symp.*, 353, (1992).

R.L. Baer et al., "STW Chemical Sensors", *Proc. IEEE Ultrasonic Symp.*, 293–298 (1992).

R.M. White, "Surface Elastic Waves" *Proc. IEEE*, 58, 1238–1276 (1970).

B.A. Auld et al., "Surface Transverse Wave Propagation Under Metal Strip Gratings", *Proc. IEEE Ultrasonic Symp.*, 261, (1986).

C. Campbell, "Surface Acoustic Wave Devices and Their Signal Processing Applications", *Academics Press Inc.*, (1989) (Chapter 18).

M.P. Thompson et al., "Epitaxial Growth of Zinc–Blende AlN on Si (001) Substrates by Plasma Source Molecular Beam Epitaxy", *Proceedings of Spring Materials Research Society, San Francisco, CA*, vol. 570, pp. 297–302 (1999).

G.W. Auner et al. "Microstructure of Low temperature grown AlN thin films on Si (111)" *J. Appl. Phys.*, 85, 7879 (1999).

S. Ballandras et al., "New Results on Surface Transverse Wave Resonators Built with Different Combinations of Groove and Strip Gratings", *IEEE Ultrasonics Symp. Proc.*, 217, 1998.

L.J. Patgridge, "Production of Catalytic Antibodies Using Combinatorial Libraries", *Biochem Soc Trans.*, 21(4), 1096 (1993).

P.K. Kuo et al., "Generation of a Large Combinatorial Library of the Immunoglobulin Repertoire in Phage Lambda", *Science*, 246, 1275 (1989).

M. Tom–Moy et al., "Atrazine Measurements Using Surface Transverse Wave Devices", *Anal. Chem.*, 1510–1516, (1995).

Zhao, Q. et al., "Development of Wide Bandgap Semiconductor Photonic Device Structures By Excimer Laser Micromachining", *MRS Internet J. Nitride Semicond. Res.*, 5S1, W11.69 (2000).

Auner, G.W., et al., "Characterization of Aluminum Nitride Thin Films Grown by Plasma Source Molecular Beam Epitaxy", 362, *SPIE* vol. 2428.

Krupitskaya, R.Y. "Optical Characterization of AlN Films Grown by Plasma Source Molecular Beam Epitaxy", *J. Appl. Phys.*, vol. 84(5), 2861, (1998).

ed. Devices J.H., and Long, A.R., "Physics of Nanostructure," *Institute of Physics Publishing, Philadelphia*, 1992.

Gourley, P.L., "Nanolasers," *Scientific American*, Mar. 1998.

Zhao, Q., et al., "Development of Wide Band Gap Semiconfuctor Photonic Device Structures by Excimer Laser, Micormachining." *Mat. Res. Soc. Proceedings*, vol. 595, W11.69.1, 2000.

P.K. Kuo. G.W. Auner and Z.L. Wu, "Microstructure and thermal conductivity of epitaxial AlN thin films" *Thin Film Solids*, 253, 223 (1994).

G.W. Auner et al., "Epitaxial Growth of AlN by Plasma Source Molecular Beam Epitaxy" in Wide Bandgap Electronic Materials, (edited by M.A. Prelas), 329–334, (Kluwer Academic Publishers, 1995).

J. Rizzo and J. Wyatt, "Prospects for a Visual Prosthesis", *The Neuroscientist*, vol. 3, No. 4 (1997).

Oh, S.H., et al., "Comparative Kinetic Studies of $CO-O_2$ and CO—NO Reactions over Single Crystal and Supported Rhodium Catalysts," *J. Catalysis*, 100, 360, 1986.

Ng, K.Y.S., et al., "NO—CO Activity and Selectivity over a $Pt_{10}Rh_{90}(111)$ Alloy Catalyst in the 10–torr Pressure Range," *J. Catalyis*, 146, 349, 1994.

Cox, D.M., et al., "Gold Clusters—Reactions and Deuterium Uptake" *Zeitschirift Fur Physik D–Atoms Molecules and Clusters*, vol. 19 (1–4), 353, 1991.

Heiz, U., et al., "CO Chemisorption on Monodispersed Platinum Clusters on SiO2 Detection of CO Chemisorption on Single Platinum Atoms," *Journal of Physical Chemistry*, 99(21), 8730, 1995.

Haruta, M., "Size–and support–dependency in the catalysis of gold," *Catalysis Today*, 36(1), 153, 1997.

Chianelli, R.R., et al., "Synthesis, Fundamental Properties and Applications of Nancrystals, Sheets, Nanotubes, and Cylinders based on Layered Transition Metal Chalcogenides," *Materials Technology*, 15(1), 35–84, 2000.

Chianelli, R.R., et al., "Fundamental Studies of Transition–metal Sulfide Catalytic Materials," *Advances in Catalysis*, 40, 177, 1994.

Reetz, M.T., et al., "Visualization of Surfactants on Nanostructured Palladium Clusters by a Combination of STM and High–resolution TEM," *Science*, vol. 267, pp. 367–369, 1995.

Xu,H., and Ng, K.Y.S., "STM Study of Oxygen on Rh(111)." *Surface Science*, 375, 161, 1997.

Serina, F., et al., Pd/AlN/SiC thin–film devices for selective hydrogen sensing AP, *Apl. Phys. Lett.*, 79 (20): 3350–3352(2001).

Serina, F., et al., Pd/AlN/Si of SiC Structure for Hydrogen Sensing Device, *Mat. Res. Soc. Symp.*, vol. 622, Ti.3.1(2000).

Kryder M.H., "Ultra high density recording technologies," *MRS Bull.*, vol. 21, (9), 17 (1996).

Chou , S., et al., "Nanolithographically defined magnetic structures and quantum magnetic disk", *J. Appl. Phys.*, 79, 6101 (1996).

Leslie–Pelecky, D.L.and Rieke, R.D., "Magnetic Properties of Nanostructured Materials" *Chem. Mater.*, 8, 1770–1783, 1996.

Wittborn, J., et al., Magnetic domain and domain wall imaging of submicron Co dots by probing the magnetostrictive response using atomic force microscopy, *Appl. Phys. Lett.*, vol. 76, No. 20 2931 (2000).

International Search Report to international Application PCT/US03/11775.

International Search Report to International Application PCT/US03/11773.

Thompson, D.F. et al., "Surface Transverse Wave Propagation Under Metal Strip Gratings", Proc. IEEE Ultrasonic Symp., Nov. 1986, 261–265.

SELF-ASSEMBLED NANOBUMP ARRAY STUCTURES AND A METHOD TO FABRICATE SUCH STRUCTURES

RELATED APPLICATION INFORMATION

This application claims the benefit of and priority to co-pending U.S. patent application Ser. No. 10/125,031, entitled "Apparatus, Method and System for Acoustic Wave Sensors Based on AlN Thin Films", filed Apr. 17, 2002, the disclosure of which is incorporated by reference in its entirety herein.

FIELD OF THE INVENTION

The present invention relates to laser assisted spontaneously formed nanobump array structures and a method for making such structures.

BACKGROUND INFORMATION

It is believed that technological barriers may exist for fabricating functional device structures with characteristic dimensions below 1 μm. These barriers may include problems in synthesizing the nano-sized structures in a sufficiently small dimension, in a specific pattern, or in a uniform size and spacing distribution. Furthermore, such nano-sized structures may require direct fabrication into microsystems to allow proper functioning. For example, a neural stimulatory microsystem may require fairly uniform nano-sized electrode arrays for use in focally stimulating neural tissue to treat blindness, as well as Parkinson disease, Huntington disease, and other neurological disorders. In one particular application, focal stimulation may require electrodes or groups of electrodes on the order of 100 nanometers or less, with spacing of no more that 5 microns to properly mimic the actions of rods and cones in the retina of the eye. Thus, overcoming the barriers to fabricating nano-sized structures may lead to developing a useful prosthesis device to restore lost vision associated with certain eye diseases, such as, for example, retinitis pigmentosa and perhaps macular degeneration.

Another difficulty in developing a controllable synthesis technology for making nano-sized structures may be attributed to the lack of systematic atomic level characterizations at various stages of the process. Detailed information regarding the geometric arrangement, lattice parameter, magnetic, electronic, and catalytic properties may be needed to understand the relationship between nanoscopic structures and their macroscopic properties. Additionally, the inability to obtain localized topographic, chemical, magnetic, and electronic information may further limit the realization of specific nanostructure characteristics.

It is believed that there have been efforts that have focused on single crystal surface studies to better understand the fundamental reaction mechanism, and to mimic the behavior of real catalysts. Such an approach is referred to in Oh, S. H., Fisher, G. B., Carpenter, J. E., and Goodman, S. W., "Comparative Kinetic Studies of Co—$O_2$ and Co—NO Reactions over Single Crystal and Supported Rhodium Catalysts," J. Catalysis, 100, 360, 1986 ("the Oh reference") and Ng, K. Y. S., Belton, D. N., Schmieg, S. J., and Fisher, G. B., "NO—CO Activity and Selectivity over a $Pt_{10}Rh_{90}(111)$ Alloy Catalyst in the 10-torr Pressure Range," J. Catalysis, 146, 349, 1994 ("the Ng reference"). The Oh and Ng references indicate that the rate constants obtained from these single crystal surfaces may be used to model the reaction rates of high surface area catalysts. Such single crystal surface studies, however, merely represent the exposure of one crystal orientation, which foregoes potential opportunities offered by cluster-size effects.

It is believed that experiments have been performed to demonstrate the benefits of cluster-size effects. Such experiments may include the use of laser ablation and mass spectrometry to produce isolated clusters in a gas phase with a specific quantity of atoms, as referred to in Cox, D. M., Brickmnan, R., Creegan, K., and Kaldor, A., "Gold Clusters—Reactions and Deuterium Uptake," Zeitschirift Fur Physik D-Atoms Molecules and Clusters, 19(1–4), 353, 1991 ("the Cox reference") and Heiz U., Sherwood, R., Cox, D. M., Kaldor, A., and Yates, J. T., "CO Chemisorption on Monodispersed Platinum Clusters on $SiO_2$ Detection of CO Chemisorption on Single Platinun Atoms," Journal of Physical Chemistry, 99(21), 8730, 1995 ("the Heinz reference"). These references have indicated that for a certain unique number (N) of atoms in the cluster, the activity and/or selectivity may be orders of magnitude higher than clusters with a different number of atoms in the cluster. Gold nano-clusters, for example, with diameters less than 5 nanometers may have been developed by the Osaka National Research Institute. As referred to in Haruta, M., "Size- and Support-dependency in the Catalysis of Gold," Catalysis Today, 36(1), 153, 1997 ("the Haruta reference"), such gold nano-structures may exhibit extraordinarily high activity and/or selectivities in a variety of reactions, including the reactions of CO and hydrogen oxidation, decomposition of amines and organic halogenated compounds, and reduction of nitrogen oxides, among others.

Two dimensional macromolecular structures of $MoS_2$ and $WS_2$ in the form of nanotubes and cylinders are referred to in Chianelli, R. R., Berhault, G., Santiage, P., Mendoza, D., Espinosa, A., Ascencio, J. A., Yacaman, M. J., "Synthesis, Fundamental Properties and Applications of Nanocrystals, Sheets, Nanotubes, and Cylinders based on Layered Transition Metal Chalcogenides," Materials Technology, 15(1), 54, 2000 ("the Chianelli reference"). The edge sites and basal plane sites of theses structures may have distinctive catalytic behavior including special activities and/or selectivities, as referred to in Chianelli, R. R., Daage, M., and Ledoux, M. J., "Fundamental Studies of Transition-metal Sulfide Catalytic Materials," Advances in Catalysis, 40, 177, 1994 ("the Daage reference").

Furthermore, efforts to use various chemical synthetic approaches to produce uniform nano-crystallites may involve the use of sol-gel processing, controlled reduction in micro-emulsions, and electrochemical reduction, as referred to in Reetz, M. T. Heilbig, W., Quaiser, S. A., Stimming, U., Breuer, N., and Vogel, R., "Visualization of Surfactants on Nanostructured Palladium Clusters by a Combination of STM and High-resolution TEM," Science, 267, 367, 1995 ("the Reetz reference"). Such efforts may, however, result in a distribution of particle size that may preclude a well-defined surface for activity-selectivity studies. Without a uniform surface, the nature of active sites may not be fully elucidated because the true catalytic active sites may constitute a very minute portion of the surface.

It is therefore believed that these studies demonstrate a need for improved methods for fabricating nano-scale catalytic devices. The challenges to fabricate such nano-sized catalysts may, however, include the ability to produce sufficiently stable structures and/or control their synthesis when using the above cited approaches. Although there may have been some ability to produce monodispersing nano-particles in solution, it is believed that dispersing these particles on a support surface in a uniform manner is problematic and therefore a challenge. Accordingly, it is believed that a need may exist for uniform and stable nano-sized catalyst device structures and a method to fabricate them.

It is also believed that the trend toward miniaturizing magnetic recording media may pose further challenges, as well as opportunities, for applications involving nano-sized structures. As referred to in Kryder, M. H., "Ultra High Density Recording Technologies", MRS Bull. Vol. 21, (9), 17(1996) ("the Kryder reference"), it has been predicted that the density of magnetic recording may reach 10 to 100 Gbits/inch during the years between 2001 and 2005. The magnetic particles in the next generation magnetic recording materials may therefore need to be ever smaller, which may be on the order of approximately 10 nanometers in size, while also remaining magnetically "hard" and moderately isolated.

With the miniaturization of magnetic technologies, the need to understand magnetization on this small scale may become increasingly important as referred to in Chou, S. Y., Kraus, P. R., and Kong, L., "Nanolithographically defined magnetic structures and quantum magnetic disk", J. Appl. Phys. 79, 6101 (1996) ("the Chou reference") and Leslie-Pelecky, D. L., Rieke, R. D., "Magnetic Properties of Nanostructured Materials", Chem. Mater. 1996, 8, 1770–1783 ("the Leslie-Pelecky reference"). The Leslie-Pelecky reference may suggest that the need to study the static and dynamic magnetic properties of nano-sized structures may be critical to their realization, particularly in the context of regular dot arrays. Major impediments to understanding the cooperative effects on the nanometer scale may include, for example, the ability to fabricate well-controlled magnetic nano-sized structures. Also, recent advances in characterizing and controlling grain size and intergranular distance of the magnetic materials may generate interest in exploring new synthesizing techniques, in which the orientation and crystalline structure of magnetic nano-sized crystals may be precisely influenced. In particular, it is believed that a fabrication technique to control these structural parameters, orientation and crystalline structure of magnetic nano-sized crystals may be especially desirable.

During the "Eye and the Chip" Symposium on Artificial Vision (Jun. 16 & 17, 2000), Dr Gregory W. Auner gave a conference in which he displayed a picture of a nanostructure formation, and indicated that work was progressing in this area towards achieving a suitable construction for retinal implantation.

SUMMARY OF THE INVENTION

An exemplary embodiment and/or exemplary method according to the present invention includes a self-assembled nanobump array structure produced from a semi-absorbing outer layer provided on at least one nanobump-forming substrate layer, the semi-absorbing outer layer is configured to ablate slowly to allow an applied laser energy to be transmitted to the at least one nanobump-forming substrate layer, in which an energy and a pressure buildup occurs in the at least one nanobump-forming substrate layer to a form the nanobump array structure.

Another exemplary embodiment and/or exemplary method is directed to providing the self-assembled nanonbump array structure, in which the self-assembled nanonbump array structure formation is uniform in size and spaced over a wide area.

Still another exemplary embodiment and/or exemplary method is directed to providing the self-assembled nanobump array structure, in which the semi-absorbing outer layer is provided via a plasma source molecular beam epitaxy system process.

Yet another exemplary embodiment and/or exemplary method is directed to providing the self-assembled nanobump array structure, in which the semi-absorbing outer layer includes a wide bandgap semiconductor material.

Still another exemplary embodiment and/or exemplary method is directed to providing the self-assembled nanobump array structure, in which the wide bandgap semiconductor material includes aluminum nitride.

Yet another exemplary embodiment and/or exemplary method is directed to providing the self-assembled nanobump array structure, in which the at least one nano-forming substrate layer includes doped silicon carbide.

Still another exemplary embodiment and/or exemplary method is directed to providing the self-assembled nanobump array structure, in which the at least one nano-forming substrate layer includes a plurality of sequential metal layers.

Yet another exemplary embodiment and/or exemplary method is directed to providing the self-assembled nanobump array structure, in which the at least one nano-forming substrate layer includes a plurality of metallic elements.

Still another exemplary embodiment and/or exemplary method is directed to providing the self-assembled nanobump array structure, in which the applied laser energy is slightly less than a bandgap energy of the semi-absorbing outer layer.

Yet another exemplary embodiment and/or exemplary method is directed to providing the self-assembled nanobump array structure, in which the laser energy has a wavelength of 248 nanometers.

Still another exemplary embodiment and/or exemplary method is directed to providing the self-assembled nanobump array structure, in which the laser energy is provided by an Excimer laser.

Yet another exemplary embodiment and/or exemplary method is directed to providing the self-assembled nanobump array structure, in which the self-assembled nanobump array structure is integrated into a neural stimulation arrangement.

Still another exemplary embodiment and/or exemplary method is directed to providing the self-assembled nanobump array structure, in which the self-assembled nanobump array structure is integrated with an electron emission arrangement.

Yet another exemplary embodiment and/or exemplary method is directed to providing the self-assembled nanobump array structure, in which the self-assembled array structure is integrated into a magnetic recording media arrangement.

Still another exemplary embodiment and/or exemplary method is directed to providing the self-assembled nanobump array structure, in which the self-assembled array structure integrated with a catalytic arrangement.

Yet another exemplary embodiment and/or exemplary method is directed to providing the self-assembled nanobump array structure, in which the catalytic arrangement includes at least one of $Al_2O_3$, $SiO_2$, and $TiO_2$.

Another exemplary embodiment and/or exemplary method is directed to fabricating a nanobump array structure by depositing a wide bandgap semiconductor material upon a substrate to form a composite layered structure and irradiating the composite layered structure with laser energy, in which the wide bandgap semiconductor material slowly ablates allowing most of the laser energy to be transmitted to the substrate, and an energy and a pressure buildup occurs in the composite layered structure to form the nanobump array structure.

Yet another exemplary embodiment and/or exemplary method is directed to fabricating the nanobump array structure, in which the laser energy is slightly less than a bandgap of the wide bandgap semiconductor material.

Still another exemplary embodiment and/or exemplary method is directed to fabricating the nanobump array structure, in which the bandgap of the wide bandgap semiconductor material is about 6.2 eV.

Yet another exemplary embodiment and/or exemplary method is directed to fabricating the nanobump array structure, in which the laser energy has a wavelength of 248 nanometers.

Still another exemplary embodiment and/or exemplary method is directed to fabricating the nanobump array structure, in which the composite layered structure is irradiating using an Excimer laser.

Yet another exemplary embodiment and/or exemplary method is directed to fabricating the nanobump array-structure, in which the wide bandgap semiconductor material includes aluminum nitride.

Still another exemplary embodiment and/or exemplary method is directed to fabricating the nanobump array structure, in which the substrate includes a layer of doped silicon carbide (SiC).

Yet another exemplary embodiment and/or exemplary method is directed to fabricating the nanobump array structure, in which the substrate includes a plurality of layers.

Still another exemplary embodiment and/or exemplary method is directed to fabricating the nanobump array structure, in which the substrate includes a layer of Au and a layer of SiC.

Yet another exemplary embodiment and/or exemplary method is directed to fabricating the nanobump array structure, in which the substrate includes a layer of Pt and a layer of Pd.

Still another exemplary embodiment and/or exemplary method is directed to fabricating the nanobump array structure, in which the substrate includes a plurality of metallic elements.

Yet another exemplary embodiment and/or exemplary method is directed to integrating the nanobump array structure with a catalytic arrangement.

Still another exemplary embodiment and/or exemplary method is directed to fabricating the nanobump array structure, in which the catalytic arrangement includes at least one of $Al_2O_3$, $SiO_2$, and $TiO_2$.

Yet another exemplary embodiment and/or exemplary method is directed to integrating the nanobump array structure into a neural stimulation arrangement.

Still another exemplary embodiment and/or exemplary method is directed to integrating the nanobunp array structure with an electron emission arrangement.

Yet another exemplary embodiment and/or exemplary method is directed to integrating the nanobump array structure into a magnetic recording media arrangement.

Still another exemplary embodiment and/or exemplary method, in which the depositing of the wide bandgap semiconductor is provided by a plasma source molecular beam epitaxy system process.

Yet another exemplary embodiment and/or exemplary method in which the plasma source molecular beam epitaxy system process includes pressurizing a growth chamber to a first level of pressurization, venting a load lock chamber to a second level of pressurization, mounting the substrate onto a substrate holder, equalizing a pressure in the growth chamber and the load lock chamber, arranging the substrate towards a PSMBE source at a distance of approximately 25 cm, sealing the growth chamber, activating a cooling arrangement of the plasma source molecular beam epitaxy system, heating a gas purifier arrangement to an operating temperature of 400° C. to 800° C., introducing a gas into the gas purifier arrangement, heating the substrate to about 650° C., rotating the substrate to a speed of approximately of one to ten revolutions per minute, closing a shutter between the substrate and the PSMBE source, activating a power supply to the PSMBE source, introduce the gas into the growth chamber, establishing an equilibrium pressure between the growth chamber and a mass flow control arrangement, igniting the PSMBE source, decreasing the pressure in the growth chamber and increasing an output of the power supply in response to a plasma formation, applying a bias potential to the substrate holder, and opening the shutter to permit growth of the wide bandgap semiconductor.

DETAILED DESCRIPTION

Figure 1A:
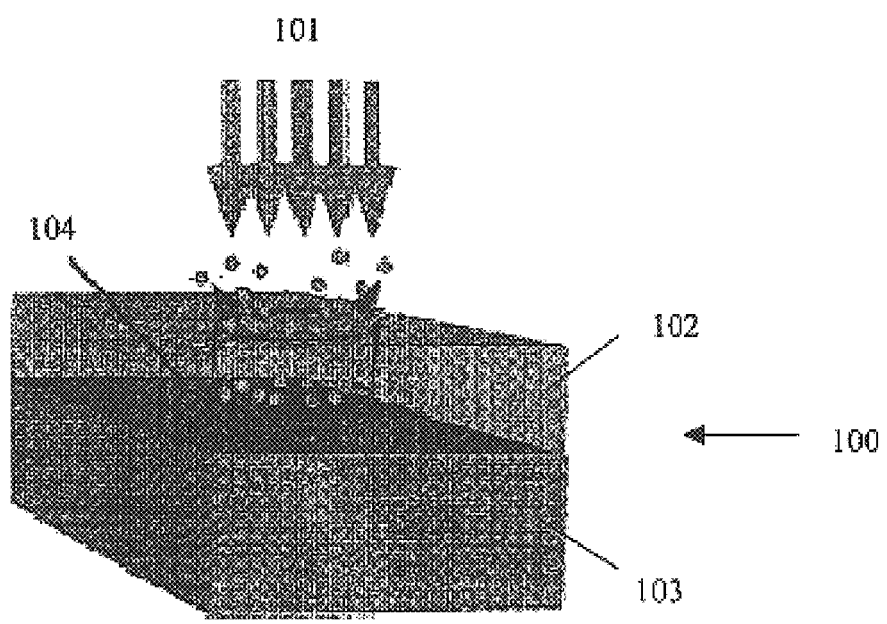
FIG. 1A shows an exemplary arrangement or structure according to the present invention in which lasers are used to form nanobump structures spontaneously.

The exemplary embodiments and/or exemplary methods of the present invention involve using a laser to irradiate composite layered structures to induce a spontaneous formation of nano-sized array structures in a controllable manner. The micro and/or nano-sized array structures (that is, the "nanobumps") arise from the layered composites during ablation of a semi-absorbing outer layer. The laser includes, for example, an Excimer laser. Furthermore, the exemplary method may involve depositing a wide bandgap semiconductor material upon one or more underlying substrate layers to form the composite-layered structure. The laser energy is then applied to the composite layered structure using an Excimer laser at a predefined wavelength. If the applied laser energy is slightly below the bandgap of the deposited wide bandgap semiconductor material, a partial or semi-absorption of the laser energy may occur in the deposited material. The semi-absorbing wide bandgap semiconductor material comprising the outer layer of the composite structure slowly ablates allowing most of the laser energy to pass to the underlying substrate layer(s), which causes an energy and pressure buildup in the underlying substrate layer(s). The result is spontaneous formation of self-assembled nanobump structures (having what is believed to be remarkable regularity in size and spacing) produced over a wide area.

The self-assembled nanobump structures may be produced, for example, on $Si^3$, on silicon carbide (SiC), and in a number of other wide bandgap semiconductors as well as metals and alloys, including aluminum nitride (AlN). These nanobump structures are expected to be applied to fabricate a new class of nano-structured semiconductors (such as, for example, Si, SiC, etc.) and nano-structured metals/alloys (such as, for example, Pt, Pd, Fe, $IrO_2$, Co, Ni, etc.) for use in various applications, such as in the integration with microsystem devices used in neural stimulation, electron emission, catalyst formation, and magnetic recording media applications. For example, the wide bandgap of aluminum nitride (AlN) at 6.2 eV may lend itself to a high cohesive energy, which may provide an inert and stable crystalline structure. In particular, the dangling bonds of the outermost surface of aluminum nitride (AlN) may form a stable passivated oxide layer and may be grown to near atomic smoothness. This combination may provide a biocompatible material that is suitable for neural implants.

The exemplary embodiments and/or exemplary methods also involve using a deposition method of plasma source molecular beam epitaxy (PSMBE) to prepare the wide bandgap aluminum nitride (AlN) semiconductors at low temperatures. The plasma source molecular beam epitaxy (PSMBE) deposition method may include the use of a magnetically enhanced hollow cathode deposition source for growing the wide band gap aluminum nitride (AlN) semiconductors. The exemplary embodiments and/or exemplary methods also involve using an excited dimmer (Excimer) laser micro-machining arrangement or setup to develop the nanobump array structures.

Figure 1B:
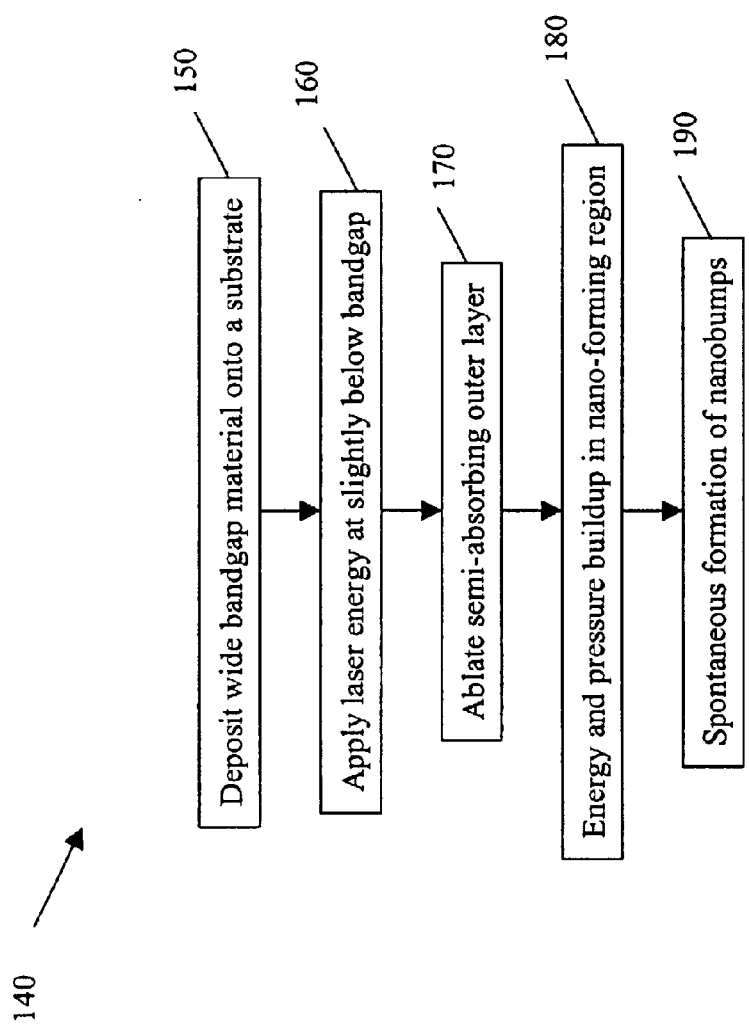
FIG. 1B shows an exemplary method involving the arrangement of FIG. 1A.

FIGS. 1A and 1B show an exemplary arrangement 100 and method 140 for fabricating or producing the laser-induced nanobump structures. In step 150, a wide bandgap semiconductor material (such as, for example, an aluminum nitride (AlN) semiconductor with a bandgap of 6.2 eV) is applied to a substrate (consisting of, for example, doped silicon carbide (SiC)) using plasma source molecular beam epitaxy (PSMBE) to form a composite structure 100 having an outer layer 102 made from the wide bandgap semiconductor material and one or more underlying substrate layers 103. In step 160, radiation 101 is applied to the composite structure 100 using, for example, an Excimer laser at a predefined wavelength (in particular, for example, 248 nm) such that the applied laser energy is slightly below the bandgap of the semiconductor material forming the outer layer 102. In step 170, the outer layer 102 is slowly abated to allow most of the laser energy to be transmitted to an underlying nano-forming region 104 between the semi-absorbing outer layer 102 and the substrate layer(s) 103. As the laser energy ablates through the semi-absorbing outer layer 102, an energy and pressure buildup occurs in the underlying nano-forming region 104 in step 180. The result, in step 190, is a spontaneous self-assembled nanobump structure of uniform size and spacing produced over a wide area (such as, for example, an area of 2 mm which may be reproduced side by side for a larger area array).

Figure 1C:
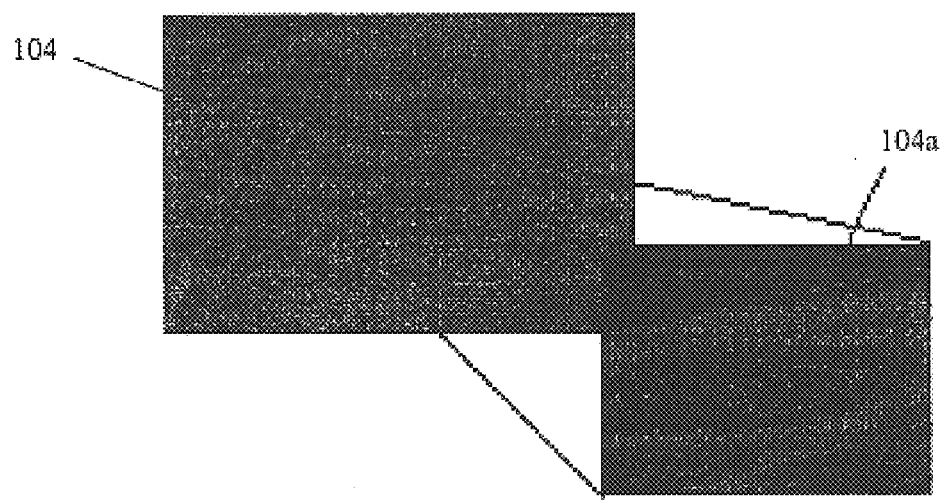
FIG. 1C shows a Scanning Electron Microscope (SEM) image of doped silicon carbide (SiC) nanobump structures fabricated using the exemplary arrangement and exemplary method of FIGS. 1A and 1B.

FIG. 1C shows a Scanning Electron Microscope (SEM) image of doped silicon carbide (SiC) nanobump structures 104a fabricated using the exemplary method of FIG. 1B. As shown in FIG. 1C, the spontaneously formed self-assembled nanobump structures 104a may be approximately 80 nanometers in diameter or size and spaced apart at a distance of 1–5 µm. In contrast, the ablation of the same silicon carbide (SiC) underlying substrate layer 103 without the semi-absorbing layer 102 results in a clean ablation with no nanobump structures 104.

Figure 2A:
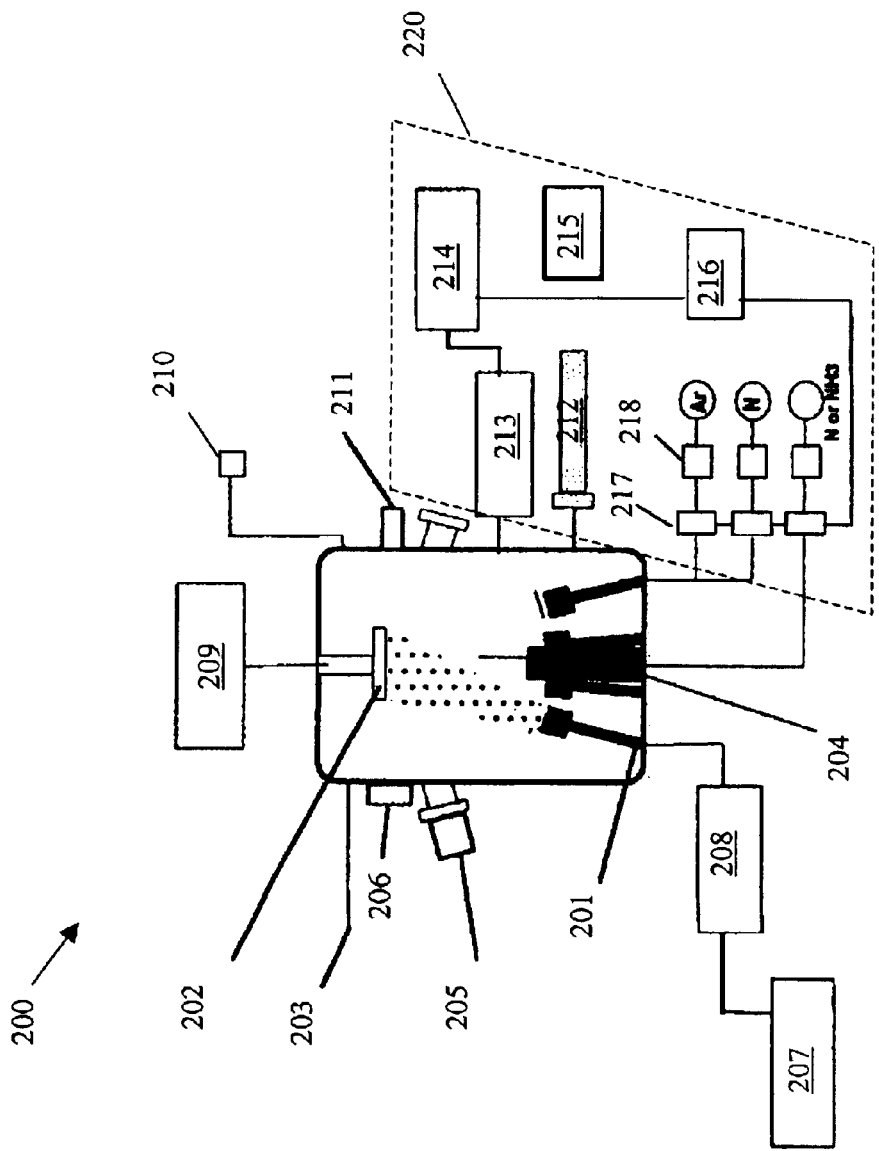
FIG. 2A shows an exemplary embodiment of a plasma source molecular beam epitaxy (PSMBE) system.

FIG. 2A shows an exemplary embodiment of a plasma source molecular beam epitaxy (PSMBE) system 200 for preparing wide bandgap materials at low temperatures. The plasma source molecular beam epitaxy (PSMBE) system 200 includes a plasma source molecular beam epitaxy (PSMBE) source 201 and a rotating heated substrate holder 202 enclosed in an ultra high vacuum (UHV) chamber 203 with a high base pressure. For example, the high base pressure may be in the upper $10^{-11}$ Torr region. Wafers (which maybe up to three inches for example) may be loaded on the rotating heated substrate holder 202.

The plasma source molecular beam epitaxy (PSMBE) system 200 may also include in-situ analytical systems, such as an infrared pyrometer 204 for measuring substrate temperatures, an optical spectrometer 205 for analyzing the plasma, a 35 kV reflective high-energy electron diffraction (RHEED) system 206 for analyzing film, and a spectroscopic ellipsometry system 207. Such analytical systems may operate in real time to provide added versatility in controlling wide bandgap semiconductor film growth in the plasma source molecular beam epitaxy (PSMBE) system 200.

The plasma source molecular beam epitaxy (PSMBE) system 200 may also include a radio frequency (RF) sputtering power supply 207 with an auto-matching network 208 connected to the plasma source molecular beam epitaxy (PSMBE) source 300, a substrate bias power supply 209 (which may be fed via the rotating substrate holder 202), a capacitance manometer 210, a 30 KeV reflective high-energy electron diffraction (RHEED) gun 211, and a mass flow control system 220. As shown, the mass flow control system 220 includes a cryopump 212, a differential pumping device 213, a residual gas analyzer 214, an ion pump 215, a controller 216, and individual mass flow arrangements 217, as well as gas purifier arrangements 218 for each element (such as, for example, argon (Ar), nitrogen (N), and ammonia (NH₃)).

Figure 2B:
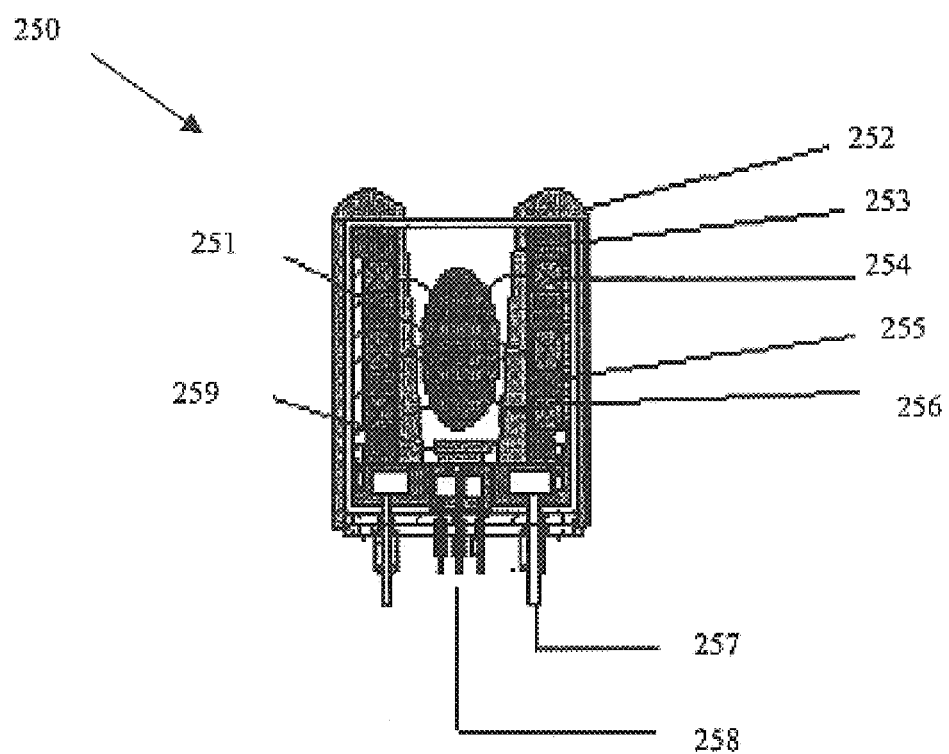
FIG. 2B shows an exemplary embodiment of a magnetically enhanced hollow cathode deposition system.

FIG. 2B shows an exemplary embodiment of the plasma source molecular beam epitaxy (PSMBE) source 201 of FIG. 2A implemented using a magnetically enhanced hollow cathode arrangement 250. A plasma 251 (which may be nitrogen or nitrogen/argon) is formed within the magnetically enhanced hollow cathode 250, which includes impeller 259 to provide an acceleration intake bias via a gas inlet 258. The walls 252 of the magnetically enhanced hollow cathode 250 are lined with a target deposition material 253. This target deposition material 253 may be molecular beam epitaxy (MBE) grade aluminum (Al) or another suitably appropriate deposition material. Magnets 254 and magnetic return 255 are provided to induce a magnetic field 256. A radio frequency (RF) or pulsed dc power 257 is coupled to the magnetically enhanced hollow cathode 250, which is intended to provide an efficient plasma formation due to the hollow cathode effect and the magnetically induced effective pressure increase.

During operation, the plasma 251 dissociates the diatomic nitrogen molecule into radical ions, as well as other combinations. The ions sputter atoms from a surface of the magnetically enhanced hollow cathode 250 (such as, for example, in a normal direction). Multiple collisions may occur before an aluminum (Al) atom or ion escapes as the nitrogen and aluminum ions are accelerated to an appropriate specific energy. The specific energy for aluminum nitride (AlN) is believed to be 12 eV. The atoms condensing onto the substrate (i.e. adatoms) may therefore have highly regulated energy. Thus, crystal growth may occur even at low substrate temperatures (such as for example, below 400° C.). Furthermore, the aluminum nitride (AlN) crystal growth may be tailored from a polycrystalline structure to near single crystalline structure, which may include both hexagonal and other-shaped structures. For example, a single high quality crystal formed using aluminum nitride (AlN) may be grown on a sapphire-based substrate.

Figure 2C:
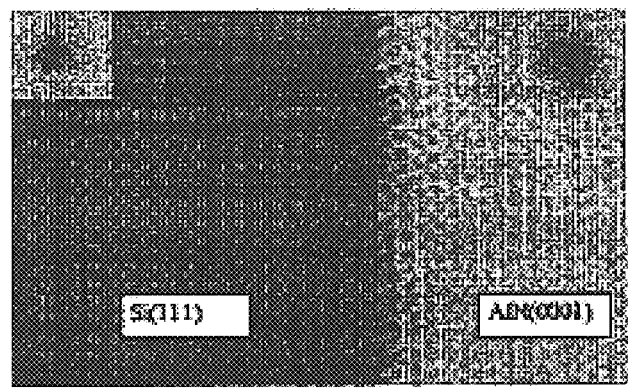
FIG. 2C shows a high resolution transmission electron micrograph of single crystal aluminum nitride (AlN) grown on a sapphire substrate using the exemplary embodiment of FIG. 2A.

FIG. 2C shows a high resolution transmission electron micrograph of single crystal aluminum nitride (AlN) grown on a sapphire substrate. The aluminum nitride (AlN) films grown on sapphire substrates may be removed to form free standing crystals by irradiating through the sapphire wafer using high energy Excimer laser pulses. The resulting films may then be micro-machined into free standing bridge structures if needed. These free standing bridge structures may be used for a variety of devices, such as, for example, accelerometers, radiation windows, and high energy UV radiation detectors.

Using the magnetically enhanced hollow cathode arrangement 200, the plasma source molecular beam epitaxy (PSMBE) source 201 may be configured to permit wide-ranging parameter control, including parameters such as the flux energy (that is, the energy ranging from thermal to high energy due to an added bias) of the depositing species achieving precise composition control. In particular, the energy may be controlled near the adatom energy level, just below the atomic displacement energy required to "knock off" covalent bonded electrons with the crystalline structure. The resulting ions may be precisely accelerated by the impeller 310 to heat the substrate to a temperature of 650° C. Maintaining an energy level that is approximately half that of the deposited crystal displacement energy (that is, the bulk crystal displacement energy), for example, is intended to better ensure maximum mobility, bond formation, ejection of contaminants, and crystal growth quality, while eliminating or at least reducing ion induced damage to the growing crystalline structure.

Figure 3A:
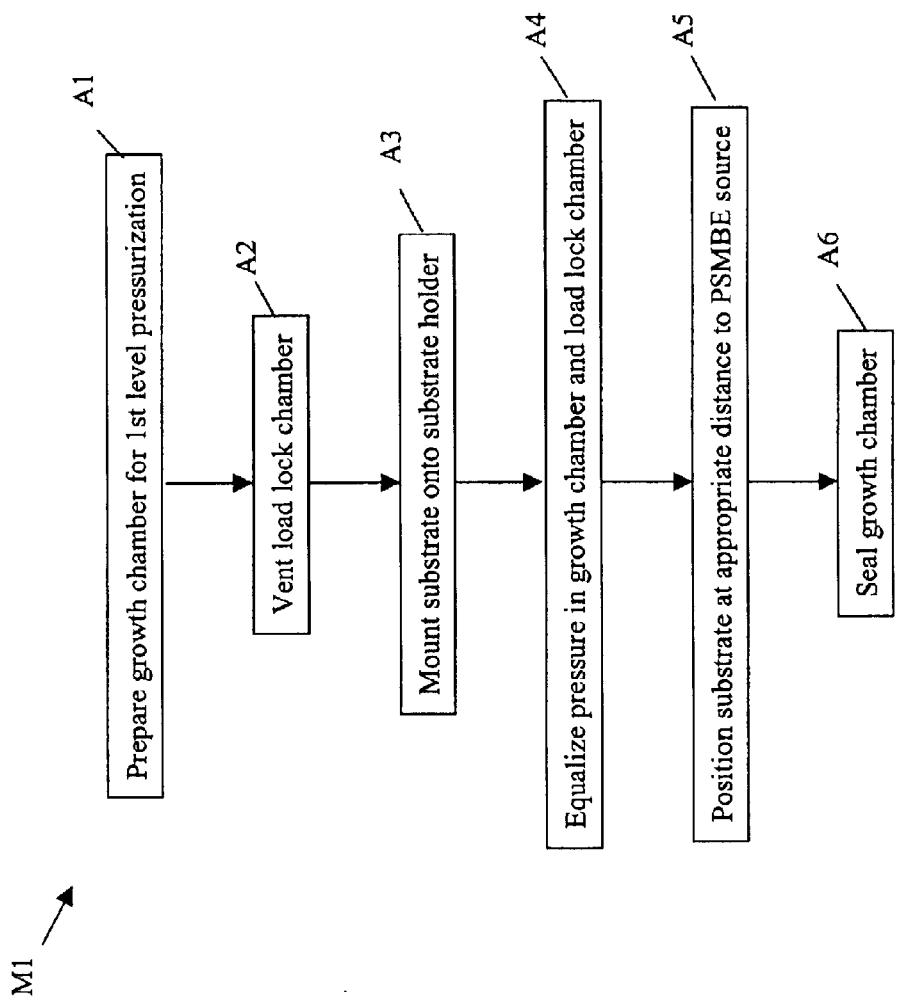
FIG. 3A shows an exemplary method to load the plasma source molecular beam epitaxy (PSMBE) system of FIG. 2A.

FIG. 3A shows an exemplary method M1 to load the plasma source molecular beam epitaxy (PSMBE) system 200 of FIG. 2A. In step A1, the ultra high vacuum (UHV) chamber 203, also known as the growth chamber, is prepared for a first level of pressurization by closing a valve between the growth chamber 203 and the differential pumping device 213, as well as closing a valve between the growth chamber 203 and a load lock chamber, and by opening a valve between the growth chamber 203 and the cryo pump 212. In step A2, a venting of the load lock chamber is performed by opening and closing a venting valve to the chamber until a pressure of approximately 750 Torr is measured. In step A3, the substrate holder 202 is mounted with a sample substrate (cleaned). In particular, the cleaned substrate may be secured via a magnetic manipulator of the substrate holder 202. In step A4, the pressure in the load lock chamber and the growth chamber 203 is equalized by closing the valve between the cryo pump and the load lock chamber, and by opening the valve between the differential pump device 213 and the load lock chamber, and by activating the differential pump device 213. When a pressure of approximately 0.00 (out of range) is measured, the valve between the growth chamber 203 and the load lock chamber may be opened. In step A5, the cleaned substrate on the substrate holder 202 is properly positioned by lowering the substrate holder 202 into the growth chamber 203 towards the PSMBE source 201 so that a distance of, for example, 25 cm is achieved between the cleaned substrate and the PSMBE source 201. In step A6, the growth chamber 203 is sealed by closing the valve between the growth chamber 203 and the load lock chamber.

Figure 3B:
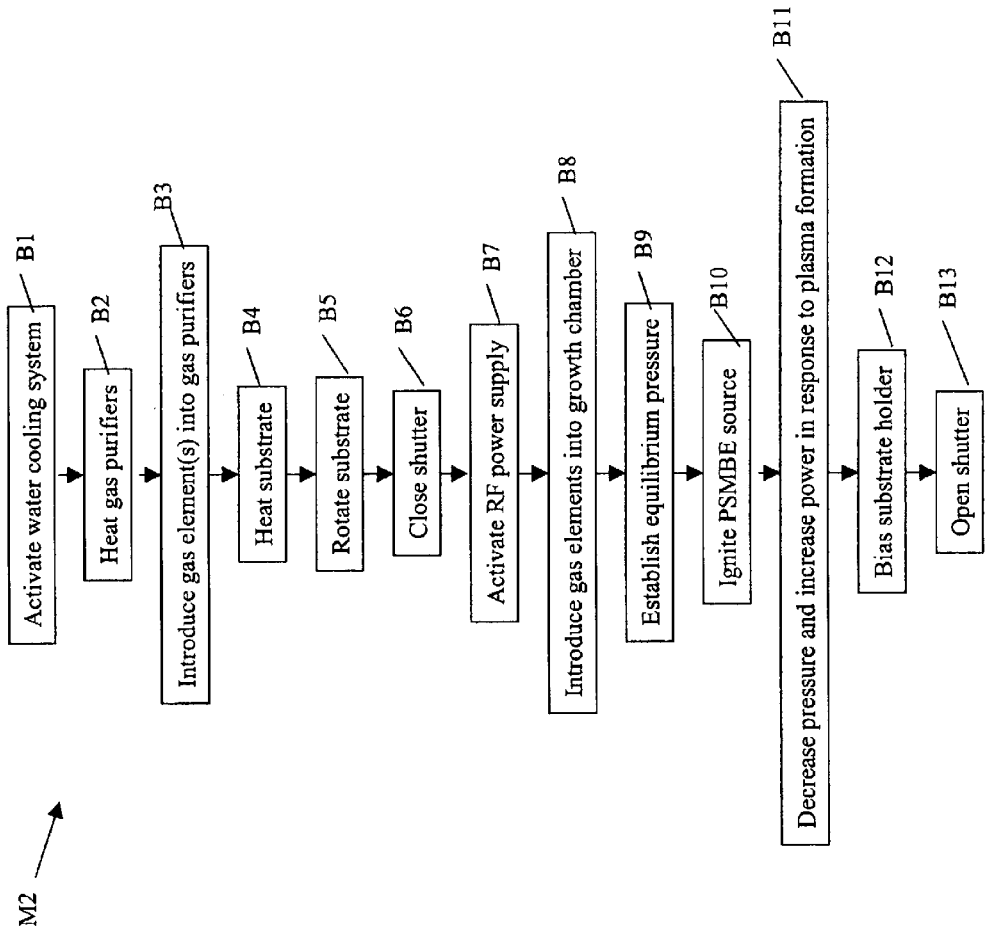
FIG. 3B shows an exemplary method to operate the plasma source molecular beam epitaxy (PSMBE) system of FIG. 2A once it has been loaded according to the exemplary method of FIG. 3A.

FIG. 3B shows an exemplary method M2 to operate the plasma source molecular beam epitaxy (PSMBE) system 200 of FIG. 2A once it has been loaded according to the exemplary method M1 of FIG. 3A. In step B1, the water cooling system is activated to a temperature of 15° C. In step B2, the gas purifier arrangements 218 of the mass flow control system 220 are activated to an operating temperature of 400° C. to 800° C. In step B3, once a gas purifier arrangement 218 achieves an appropriate operating temperature (such as, for example, 800° C. ), the appropriate gas element (such as, for example, argon (Ar), nitrogen (N), and ammonia (NH₃)) is introduced into the gas purifier arrangement 218. In step B4, the cleaned substrate on the substrate holder 202 is heated to a desired temperature (such as, for example, 650° C.). In step B5, the substrate holder 202 is rotated to a speed of approximately 1–10 revolutions per minute (RPM). In step B6, a shutter between the cleaned substrate and the PSMBE source 201 is closed to prevent premature deposition, Next, in step B7, the radio frequency (RF) sputtering power supply 207 for the PSMBE source 201 is activated. In step B8, the appropriate gas element(s) (such as, for example, argon (Ar), nitrogen (N), and ammonia (NH₃)) are introduced into the growth chamber 203 at an appropriate rate (such as, for example, a flow rate of 40 standard cubic centimeters per minute (SCCM) for Ar; a flow rate of 10 SCCM for N₂) by adjusting the appropriate individual mass flow arrangement 217. In step B9, an equilibrium pressure is established (such as, for example, 30 mTorr) between the mass flow control system 220 and the growth chamber 203 by adjusting the valve between the cryo pump 212 and the growth chamber 203. In step B10, the PSMBE source 201 is "ignited" by increasing the output of the radio frequency (RF) sputtering power supply 207 to an appropriate power level (such as, for example, 100 watts). In step B11, once a plasma 251 begins to form, the pressure within the growth chamber 203 is decreased to an appropriate operating level (such as, for example, 1 mTorr) by adjusting the valve between the growth chamber 203 and the cryo pump 212, and the output of the radio frequency (RF) sputtering power supply 207 is increased to an appropriate operating power level (such as, for example, 200 watts). In step B12, a bias voltage potential (such as, for example, −12 volts) is applied to the substrate holder 202 by adjusting the substrate bias power supply 209 so that an acceleration of ions out of the plasma 251 towards the substrate may occur. In step B13, the shutter between the substrate and the PSMBE source 201 is opened to permit a growth of a thin film onto the substrate.

Figure 3C:
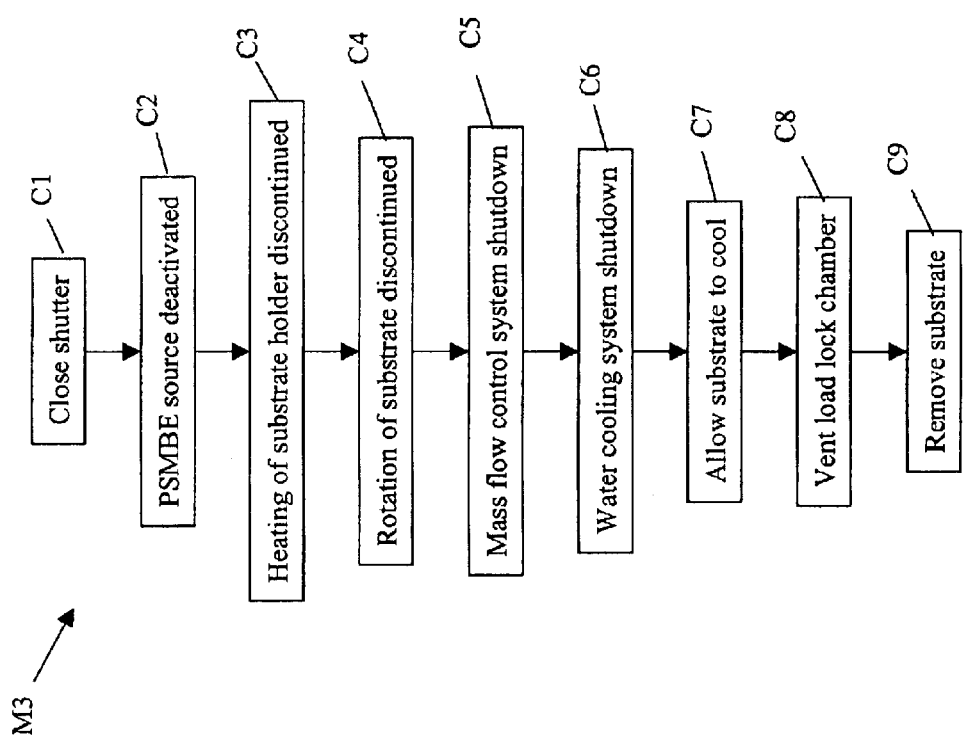
FIG. 3C shows an exemplary method to shutdown the plasma source molecular beam epitaxy (PSMBE) system of FIG. 2A once a thin film has been grown on the substrate according to the exemplary method of FIG. 3B.

FIG. 3C shows an exemplary method M3 to shutdown the plasma source molecular beam epitaxy (PSMBE) system 200 of FIG. 2A once a thin film has been grown on the substrate according to the exemplary method M2 of FIG. 3B. In step C1, the shutter between the substrate and the PSMBE source 210 is closed to prevent further deposition. In step C2, PSMBE source 201 is deactivated by shutting off the radio frequency (RF) sputtering power supply 207. In step C3, the heating of the substrate holder 202 is discontinued. In step C4, the rotation of the substrate holder 202 is discontinued. In step C5, the mass flow control system 220 is shut down by turning off the individual mass flows 217, waiting 1–2 minutes and then shutting off the gas purifier arrangement 218. In step C6, another waiting period occurs until the temperature of the substrate decreases to an appropriate temperature (such as, for example, 100° C.). In step C7, the water cooling system is shut down. In step C8, the valve between the growth chamber 203 and the cryo pump 212 is opened and a venting of the load lock chamber is performed by opening and closing a venting valve to the chamber until a pressure of approximately 750 Torr is measured. In step C9, the substrate is removed the growth chamber 203.

To develop nanobump array structures 104 for use in extending the capabilities of various biomedical Microsystems referred to herein, for example, the exemplary embodiments and/or exemplary methods of the present invention may involve the use of Excimer laser technology. Excimer lasers operate in the ultra-violet (UV) range thereby emitting high photon energy (Excimer stands for "excited dimmer", a diatomic molecule, which may be an inert gas atom and a halide atom, having a very short lifetime and dissociates releasing energy through ultra-violet (UV) photons).

Figure 4:
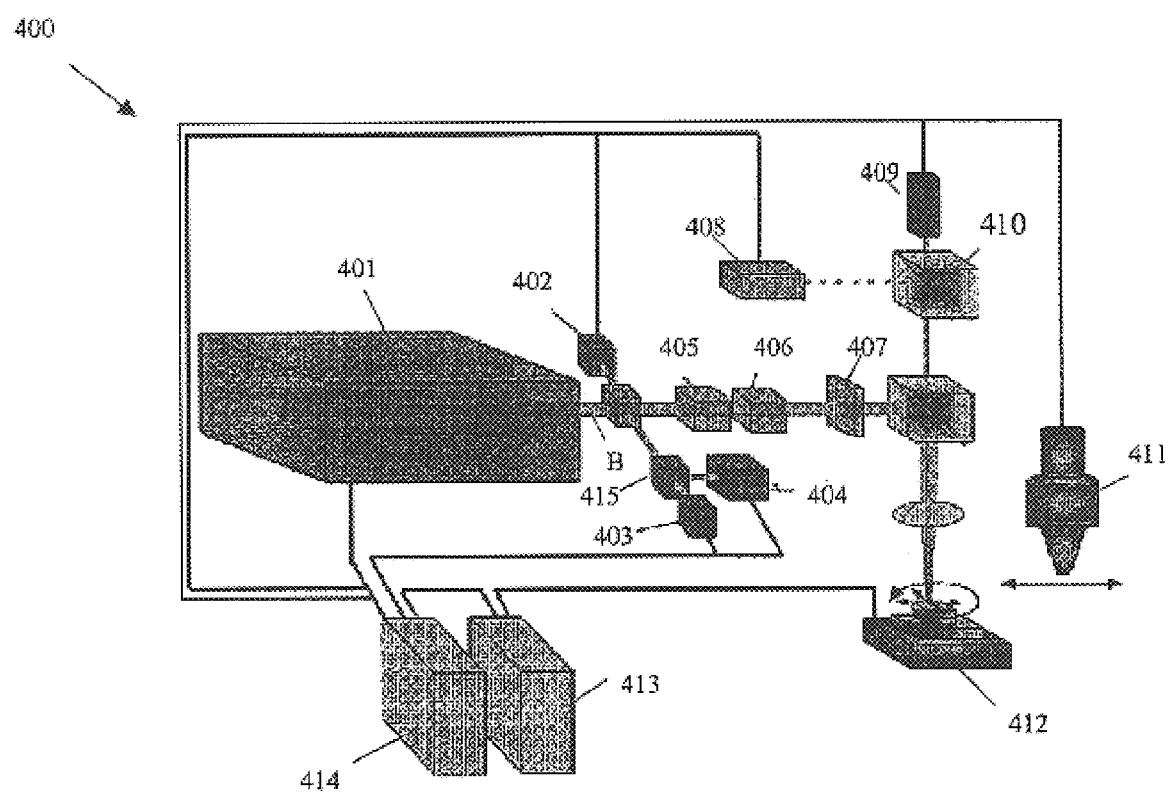
FIG. 4 shows an exemplary embodiment of an Excimer laser micro-machining arrangement.

FIG. 4 shows an exemplary embodiment of an Excimer laser micro-machining arrangement 400. As shown, the Excimer laser micro-machining arrangement 400 includes a laser source 401 (such as, for example, a Lambda Physik 200 Excimer laser), which may be operated in a KrF mode so as to emit a wavelength of about 248 nanometers, for example. Operating at this wavelength is intended to provide superior results when compared to operation at smaller emitted wavelengths. The resulting laser beam B may reach an energy level on the order of about 600 milli-Joules, for example, with a pulse duration of 25 nanoseconds and a rectangular output beam having dimensions of about 23 mm×8 mm. The laser beam B passes through a neutralized continuously tunable attenuator arrangement 405 and a homogenizer arrangement 406 having a micro-lens array arrangement. The micro-lens array arrangement of the homogenizer 406 is used to split the laser beam B into different beamlets traveling along different paths, and is also used to overlap them on a plane to be irradiated (that is, the mask 407). The gaussian beam profile of the laser beam B is then transformed to a near perfect or essentially flat-top shape (which may be a flatness of 0.87, for example).

The mask 407 is placed in the homogenized plane (with a homogenized illumination area of 18 mm×18 mm, for example) and imaged by an objective lens onto the sample. The sample is placed on top of an ultra-precision 4-dimensional scanning stage 412 (which may be, for example, a Newport PM500, X, Y, Z and rotation; X and Y with 80 mm travel limit, and 0.05 µm-linear resolution; Z with 25 mm travel limit, and 0.025 µm linear resolution; rotation stage with 360° C. travel, and 0.00030 rotary resolution). A photon beam profiler 404 is used to measure the laser beam intensity profile, a pyroelectric energy sensor 402 is used to measure the laser pulse energy and a fast-response. A photodiode 415 (such as, for example, a Hamamatsu photodiode) is used to measure the pulse time shape. A processor arrangement 414 and motion control system 413 is used to control the Excimer laser micro-machining arrangement 400. This may include control of the laser source 401, sample scanning stage to control micro-patterning design and fabrication, and laser beam characterization. The Excimer laser micro-machining arrangement 400 may also include a computer controlled display (CCD) camera 408, an alignment laser arrangement 409, a beam splitter 410, and an optical surface profiler (interferometer) 411.

According to one exemplary embodiment and/or exemplary method of the present invention, the underlying substrate layer 103 may be implemented as a multi-layered structure and/or be composed of multiple metallic elements. For example, instead of a single substrate layer 103 underlying the semi-absorbing outer layer 102 as demonstrated in FIG. 1A, one or more additional sequential layers may used. In one exemplary embodiment, a layer of Au may be followed by a layer of SiC, and in another exemplary embodiment, a layer of Pt may be followed by a layer of Pd, or vice versa. Alternatively, a single mixed layer may be provided that is formed by simultaneously depositing two metals.

Figure 5:
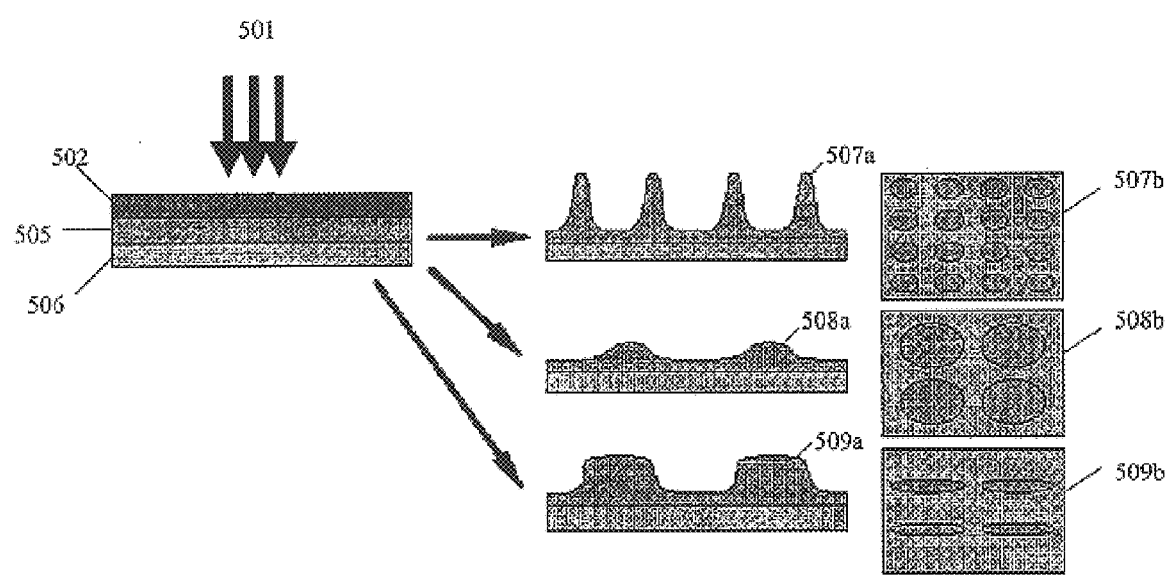
FIG. 5 shows exemplary catalyst nanobump structures fabricated using the laser-assisted nanobump forming method of FIG. 1B.

FIG. 5 shows exemplary nanobump structures 507, 508, and 509 fabricated using an exemplary multi-layer configuration method of the present invention. A thin metal layer 505 (such as, for example, Au, Pt or Pd of approximately 100 nm) is deposited on a substrate 506 (such as, for example, SiC). Next, a layer of a high quality wide-bandgap semiconductor 502 (such as, for example, an aluminum nitride (AlN) semiconductor) is deposited on the metal layer 505. By controlling the mask aperture, pulse frequency, and intensity of the Excimer laser radiation energy 501 and by adjusting the thickness of the semi-absorbing outer layer 502, various-sized nanobump structures 507, 508, or 509 may be formed with a specific spacing and pattern. For example, by adjusting the laser intensity and frequency from 20 mJ–600 mJ at 1 Hz 100 Hz, as well as the monitoring the thickness of the semi-absorbing outer layer 502, nanobump structures 507 with a base diameter as small as 25 nm may be formed. In particular, the nanobump structures are shown in a side view 507a and a top view 507b. Increasing the intensity of the Excimer laser should provide larger nanobump structures 508 having a base diameter of 80 nanometers, for example. Moreover, a ridge-like structure 509 may be provided using a succession of laser pulses while simultaneously moving the laser beam laterally. Since the laser radiation energy 501 of the Excimer laser may be controlled in a precise manner and the process is self-assembling, the formed nanobump structures 507, 508, or 509 should be stable and highly uniform in size and spacing.

The exemplary multilayer configuration method of FIG. 5 may be used, for example, to fabricate novel catalyst formulations. In particular, the self-assembling nanobump fabricating may method permit the formation of various pyramid-like structures offering a rich variety of catalytic active sites, each having a unique and/or unusual catalytic behavior. For example, the top of the pyramid structure may represent a highly unsaturated site with few atoms (such as, for example 1 to 5 atoms), the ridges may represent a row unsaturated sites (such as, for example, a [111] surface), and the four faces may represent a specific crystalline plane structure.

According to an exemplary embodiment and/or exemplary method of the present invention, the spontaneously induced nanobump array structures may be directly integrated with catalytic devices and/or may cooperate with catalyst support materials. For example, catalyst support materials may facilitate the nanobump forming process, as well as provide a high surface area for dispersing active catalyst crystallites. Such catalyst support materials may include, for example, $Al_2O_3$, $SiO_2$ or $TiO_2$. Upon application of the Excimer radiation, the oxide layer remaining after ablation is redistributed to result in uniform crystallites on an oxide surface that may be modeled as a real-life supported catalyst.

Application of the exemplary embodiments and/or exemplary methods of the present invention for model catalytic studies may have an advantage over a single crystal surface approach, which may be "flat" and which may lack a size affect. Since crystalline size may affect the activity and selectivity of structure-sensitive reactions, the new method may provide advantages over a high surface catalyst approach, which may exhibit an incomplete mono-dispersal characteristic. In addition, active catalyst particles on a high surface area catalyst may be easily aggregated or sintered, as well as being easily aggregated. The model catalysts may be characterized in an integrated Ultra High Vacuum-Scanning Tunneling Microscopy (UHV-STM) high-pressure system using appropriate probe reactions.

According to another exemplary embodiment and/or exemplary method of the present invention, the spontaneously induced self-assembled nanobump array structures 104 may be directly integrated with electron emission devices. For example, a Ti/IrTaO$_2$ coated nanobump array may be used to induce the electron emission of the structure. This method involves a series of corona points, for example, hundreds of which may make up a single pixel. The combined electron emission from the array of nanobumps may be used to form a single emission electrode, which should enhance electron emission efficiency and which should exhibit near negative electron affinity (cold emitter).

Figure 6:
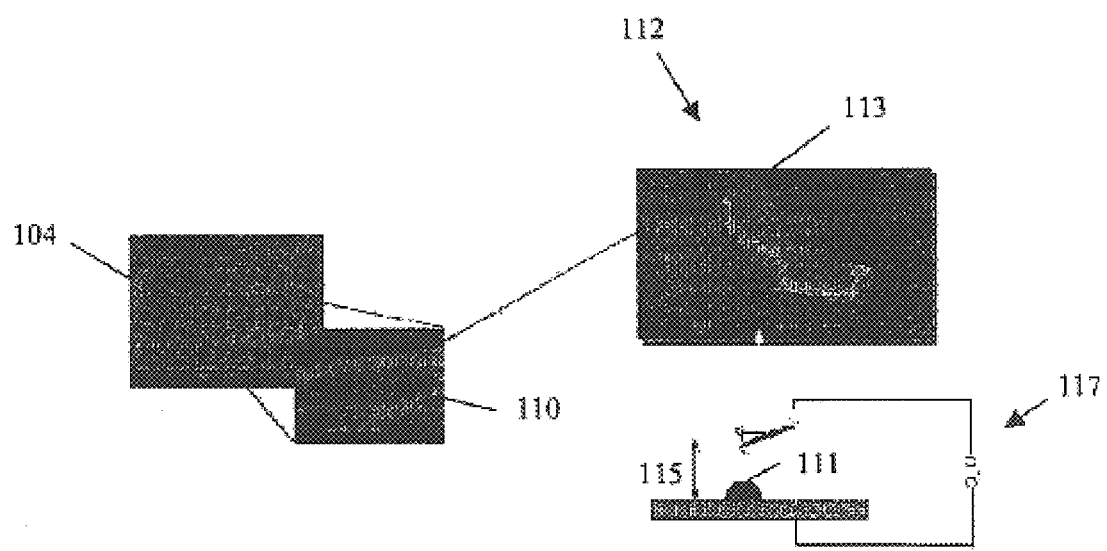
FIG. 6 shows the results of a biased atomic force microscopy experiment that indicate a charge concentration at the apex of an exemplary nanobump array structure.

FIG. 6 shows the charge concentration of an exemplary nanobump structure 110. The charge concentration is obtained using biased atomic force microscopy. A charge concentration 112 at an apex 111 of a nanobump structure 110 of a nanobump structure formation 104 may be indicated by the circuit arrangement 117, which measures, as a repulsive force, the change in distance 115. A charge concentration 113 segment indicates a maximum charge and another charge concentration segment 114 indicates little or no charge. It is believed that a charge concentration of this type is critical to developing a focally-charged neural stimulatory device for use in directly interacting with bipolar and other neural cells.

According to one exemplary embodiment and/or exemplary method of the present invention, the spontaneously induced nanobump array structures 104 may be directly integrated with neural stimulation devices. In particular, nanobump array structures of bio-compatible materials such as SiC, AlN, and a graded Ti/IrTaO$_2$ may be interfaced with retinal bipolar tissue.

Figure 7A:
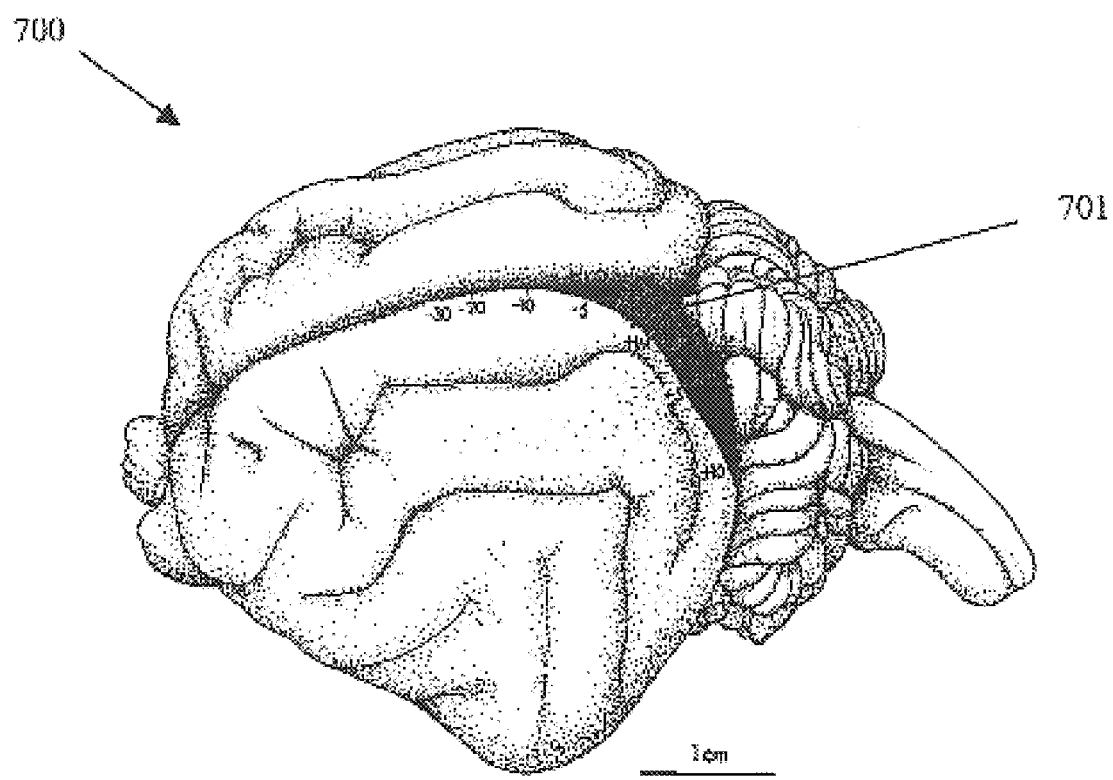
FIG. 7A shows an exemplary neurosurgical approach and placement of an exemplary multi-electrode array implant device onto the primary visual cortex in area on the dorsolateral surface of the cerebral hemisphere in a feline brain.
Figure 7B:
FIG. 7B shows an intraoperative photomicrograph demonstrating the placement of an exemplary multi-electrode array implant device along the medial bank hemisphere of a feline brain.

FIG. 7A shows an exemplary neurosurgical approach and placement of a retinal implant device onto the primary visual cortex in area 701 on the dorsolateral surface of the cerebral hemisphere in a feline brain 700. FIG. 7B shows an intra-operative photomicrograph demonstrating the location 703 of a multi-electrode array (10 mm×6 mm×1 mm) along the medial bank hemisphere. The sterile procedure involves opening the skull with a detached craniotomy, excising the dura mater, and exposing the neocortex in one cerebral hemisphere. Using the nanobump array structure of the exemplary methods and/or embodiments, implants with surface electrodes may be placed on the cerebral cortex in the region of the motor cortex or primary visual cortex, the dura mater closed over the implant sutures, and the bone flap sutured in place. An implant device in a feline may be securely positioned over most of the primary visual cortex and thus may be tested with various electrophysiological techniques. For example, the embedded implant device may be advanced vertically along the medial bank of the occipital lobe immediate juxtaposition to area 701; the falx cerebri, the bony tenorium, and the contralateral cerebral hemisphere may combine to secure the implant device in place without penetrating "tacks" or sutures; and the dura mater may be closed successfully with suture using microsurgical techniques over the dorsal surface of the cerebral hemisphere, easily securing and immobilizing leads that may emanate from the implant.

According to an exemplary embodiment and/or exemplary method of the present invention, magnetic nano-sized structures may be formed as ordered arrays of magnetic bits having various specific aspect ratios and spacing. In particular, a magnetic field may be applied to the metal layer 505 of FIG. 5 prior to application laser ablation. The resulting magnetic nano-sized structures may be used to provide a fundamental understanding of nano-magnetic properties regarding such as, for example, temperature, coercivity, anistropy, and remnant magnetization. The magnetic nano-sized structures may also have applied use in Co, FePt, and CoPt systems.

What is claimed is:

1. A self-assembled nanobump array structure comprising:
    at least one nanobump-forming substrate layer; and
    a semi-absorbing outer layer provided on the at least one nanobump-forming substrate layer, the semi-absorbing outer layer configured to ablate slowly to allow an applied laser energy to be transmitted to the at least one nanobump-forming substrate layer;
    wherein the self-assembled nanobump array structure is formed by an energy and a pressure buildup occurring in the at least one nanobump-forming substrate layer.

2. The self-assembled nanobump array structure of claim 1, wherein the self-assembled nanonbump array structure formation is uniform in size and spaced over a wide area.

3. The self-assembled nanobump array structure of claim 1, wherein the semi-absorbing outer layer is provided via a plasma source molecular beam epitaxy system process.

4. The self-assembled nanobump array structure of claim 1, wherein the semi-absorbing outer layer includes a wide bandgap semiconductor material.

5. The self-assembled nanobump array structure of claim 4, wherein the wide bandgap semiconductor material includes aluminum nitride.

6. The self-assembled nanobump array structure of claim 1, wherein the at least one nano-forming substrate layer includes doped silicon carbide.

7. The self-assembled nanobump array structure of claim 1, wherein the at least one nano-forming substrate layer includes a plurality of sequential metal layers.

8. The self-assembled nanobump array structure of claim 1, wherein the at least one nano-forming substrate layer includes a plurality of metallic elements.

9. The self-assembled nanobump array structure of claim 1, wherein the applied laser energy is slightly less than a bandgap energy of the semi-absorbing outer layer.

10. The self-assembled nanobump array structure of claim 1, wherein the laser energy has a wavelength of 248 nanometers.

11. The self-assembled nanobump array structure of claim 1, wherein the laser energy is provided by an Excimer laser.

12. The self-assembled nanobump array structure of claim 1, wherein the self-assembled nanobump array structure is integrated into a neural stimulation arrangement.

13. The self-assembled nanobump array structure of claim 1, wherein the self-assembled nanobump array-structure is integrated with an electron emission arrangement.

14. The self-assembled nanobump array structure of claim 1, wherein the self-assembled array structure is integrated into a magnetic recording media arrangement.

15. The self-assembled nanobump array structure of claim 1, wherein the self-assembled array structure integrated with a catalytic arrangement.

16. The self-assembled nanobump array structure of claim 1, wherein the catalytic arrangement includes at least one of $Al_2O_3$, $SiO_2$, and $TiO_2$.

17. A method for fabricating a nanobump array structure, the method comprising:

depositing a wide bandgap semiconductor material upon a substrate to form a composite layered structure; and irradiating the composite layered structure with laser energy;

wherein the wide bandgap semiconductor material slowly ablates allowing most of the laser energy to be transmitted to the substrate, and an energy and a pressure buildup occurs in the composite layered structure to form the nanobump array structure.

18. The method of claim 17, wherein the laser energy is slightly less than a bandgap of the wide bandgap semiconductor material.

19. The method of claim 17, wherein the bandgap of the wide bandgap semiconductor material is about 6.2 eV.

20. The method of claim 17, wherein the laser energy has a wavelength of 248 nanometers.

21. The method of claim 17, wherein the composite layered structure is irradiating using an Excimer laser.

22. The method of claim 17, wherein the wide bandgap semiconductor material includes aluminum nitride.

23. The method of claim 17, wherein the substrate includes a layer of doped silicon carbide.

24. The method of claim 17, wherein the substrate includes a plurality of layers.

25. The method of claim 24, wherein the substrate includes a layer of Au and a layer of SiC.

26. The method of claim 24, wherein the substrate includes a layer of Pt and a layer of Pd.

27. The method of claim 17, wherein the substrate includes a plurality of metallic elements.

28. The method of claim 17, further comprising:

integrating the nanobump array structure with a catalytic arrangement.

29. The method of claim 28, wherein the catalytic arrangement includes at least one of $Al_2O_3$, $SiO_2$, and $TiO_2$.

30. The method of claim 17, further comprising:

integrating the nanobump array structure into a neural stimulation arrangement.

31. The method of claim 17, further comprising:

integrating the nanobump array structure with an electron emission arrangement.

32. The method of claim 17, further comprising:

integrating the nanobump array structure into a magnetic recording media arrangement.

33. The method of claim 17, wherein the depositing of the wide bandgap semiconductor is provided by a plasma source molecular beam epitaxy system process.

34. The method of claim 33, wherein the plasma source molecular beam epitaxy system process includes:

pressurizing a growth chamber to a first level of pressurization;

venting a load lock chamber to a second level of pressurization;

mounting the substrate onto a substrate holder;

equalizing a pressure in the growth chamber and the load lock chamber;

arranging the substrate towards a PSMBE source at a distance of approximately 25 cm;

sealing the growth chamber;

activating a cooling arrangement of the plasma source molecular beam epitaxy system;

heating a gas purifier arrangement to an operating temperature of 400° C. to 800° C.;

introducing a gas into the gas purifier arrangement;

heating the substrate to about 650° C.;

rotating the substrate to a speed of approximately of one to ten revolutions per minute;

closing a shutter between the substrate and the PSMBE source;

activating a power supply to the PSMBE source;

introduce the gas into the growth chamber;

establishing an equilibrium pressure between the growth chamber and a mass flow control arrangement;

igniting the PSMBE source;

decreasing the pressure in the growth chamber and increasing an output of the power formation;

applying a bias potential to the substrate holder; and opening the shutter to permit growth of the wide bandgap semiconductor.

* * * * *